(12) United States Patent
Kawanago

(10) Patent No.: US 8,947,667 B2
(45) Date of Patent: Feb. 3, 2015

(54) SPECTROPHOTOMETER

(71) Applicant: Canon Kabushiki Kaisha, Tokyo (JP)

(72) Inventor: Hiroshi Kawanago, Utsunomiya (JP)

(73) Assignee: Canon Kabushiki Kaisha (JP)

( * ) Notice: Subject to any disclaimer, the term of this patent is extended or adjusted under 35 U.S.C. 154(b) by 0 days.

(21) Appl. No.: 13/934,459

(22) Filed: Jul. 3, 2013

(65) Prior Publication Data

US 2014/0016128 A1    Jan. 16, 2014

(30) Foreign Application Priority Data

Jul. 13, 2012    (JP) .................. 2012-157041

(51) Int. Cl.
*G01N 21/25* (2006.01)
*G01J 3/42* (2006.01)
*G01J 3/10* (2006.01)
*G01J 3/46* (2006.01)
*G01J 3/50* (2006.01)

(52) U.S. Cl.
CPC .... *G01J 3/42* (2013.01); *G01J 3/10* (2013.01); *G01J 3/465* (2013.01); *G01J 3/502* (2013.01)
USPC ........................................ 356/405

(58) Field of Classification Search
USPC .................................... 356/402–425
See application file for complete search history.

(56) References Cited

U.S. PATENT DOCUMENTS 6,535,278 B1 *   3/2003   Imura ............................ 356/73
8,288,739 B2 * 10/2012   Imura ........................ 250/461.1

FOREIGN PATENT DOCUMENTS

JP      2000-292259 A     10/2000
JP      2004-101358 A      4/2004

* cited by examiner

*Primary Examiner* — Abdullahi Nur
(74) *Attorney, Agent, or Firm* — Rossi, Kimms & McDowell LLP

(57) ABSTRACT

The spectrophotometer of the present invention measures a spectral reflectance of an object to be measured to thereby determine a color value of the object to be measured based on a color-matching function of an XYZ color system and the spectral reflectance. The spectrophotometer includes an irradiation unit configured to irradiate the object to be measured with light having a spectral intensity distribution in which a relative intensity at a wavelength at which the value of z reaches its peak in the color-matching function is equal to or greater than 0.5.

6 Claims, 5 Drawing Sheets

SPECTROPHOTOMETER

BACKGROUND OF THE INVENTION

1. Field of the Invention

The present invention relates to a spectrophotometer that measures color of an object to be measured by specifying the spectral reflection property of the object to be measured.

2. Description of the Related Art

Color measuring methods are broadly classified into two methods, i.e., a spectral colorimetry method (spectrophotometric colorimetry) and a stimulation value direct-reading method. A spectrophotometer performs color measurement using the former method. The spectrophotometer calculates tristimulus values from the spectral reflectance of an object to be measured to thereby determine the color value of various color systems standardized by CIE (International Commission on Illumination) based on these numeral values. The spectrophotometer is basically constituted by a light source that irradiates an object to be measured with light, a spectroscope that diffracts light, and a sensor that receives light. A method in which an LED (light-emitting diode) is used as the light source of the spectrophotometer is widely known. In the method, a plurality of LEDs having different spectral intensity distributions is combined with each other such that the spectral intensity distribution of the light source becomes continuous within the visible light region (see FIG. 3 disclosed in Japanese Patent Laid-Open No. 2000-292259). In the method using a plurality of LEDs, a color value to be measured may undesirably be affected by a shift of the spectral intensity distribution due to variations in the manufacture of LEDs.

In order to avoid the disadvantageous circumstance, there has been proposed a light source configuration method in which a color value to be measured is hardly affected by a shift of the spectral intensity distribution of an LED (see FIG. 10 and FIG. 11 disclosed in Japanese Patent Laid-Open No. 2004-101358). The method enables measurement with high accuracy by giving consideration to the color-matching function or the magnitude of the change in the spectral reflectance of an object to be measured upon selection of the spectral intensity distribution of an LED used for a light source.

However, although the method can improve measurement accuracy in a single spectrophotometer, the method does not consider an instrumental error which is a difference in the color value between a plurality of spectrophotometers, resulting in occurrence of variations in measured values for each device.

SUMMARY OF THE INVENTION

The present invention provides a spectrophotometer that is advantageous, for example, for reducing an instrumental error between a plurality of spectrophotometer.

According to an aspect of the present invention, a spectrophotometer that measures a spectral reflectance of an object to be measured to thereby determine a color value of the object to be measured based on a color-matching function of an XYZ color system and the spectral reflectance is provided that includes an irradiation unit configured to irradiate the object to be measured with light having a spectral intensity distribution in which a relative intensity at a wavelength at which the value of z reaches its peak in the color-matching function is equal to or greater than 0.5.

According to the present invention, a spectrophotometer that is advantageous, for example, for reducing an instrumental error between a plurality of spectrophotometers may be provided.

Further features of the present invention will become apparent from the following description of exemplary embodiments with reference to the attached drawings.

DESCRIPTION OF THE EMBODIMENTS

Hereinafter, preferred embodiments of the present invention will be described with reference to the drawings.

Figure 1:
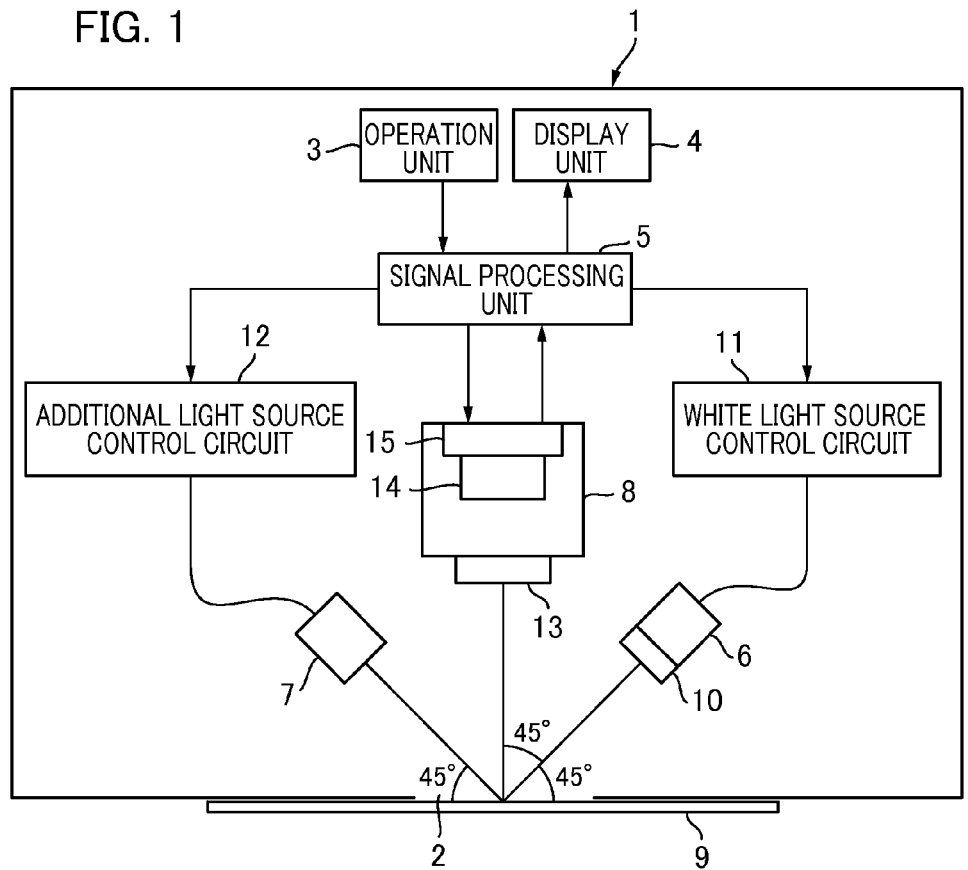
FIG. 1 is a diagram illustrating a configuration of a spectrophotometer according to one embodiment of the present invention.

Firstly, a description will be given of a spectrophotometer to which the present invention is applied. FIG. 1 is a schematic diagram illustrating a configuration of a spectrophotometer 1. The spectrophotometer 1 according to one embodiment of the present invention is a colorimetry device using a spectral colorimetry method. Firstly, the spectrophotometer 1 includes an opening 2, an operation unit 3, a display unit 4, a signal processing unit 5, a white light source (first light source) 6, a light source (hereinafter referred to as "z-approximate light source") (second light source) 7 having a spectral intensity distribution approximating the color-matching function z in an XYZ color system, and a spectroscope 8. Note that the white light source 6 and the z-approximate light source constitute an irradiation unit (not shown). Here, in the color-matching functions x, y, and z in an XYZ color system standardized by CIE, a bar (–) is normally attached to the top of each lower case letter but is omitted herein.

The opening 2 faces an object to be measured 9 upon measurement thereof. The operation unit 3 has a switch or the like, a measurement condition is set by the operation unit 3 when a measurement operation is carried out. At this time, a set value is output to the display unit 4 constituted by an LCD (liquid crystal display). The set value set by the operation unit 3 is input to the signal processing unit 5. The signal processing unit 5 is constituted by an MCU (Micro Control Unit) and outputs a control signal based on a set value.

The white light source 6 has an infrared-cut filter 10 and is connected to a white light source control circuit 11. The white light source control circuit 11 controls the white light source 6 in accordance with a control signal output from the signal processing unit 5 to thereby adjust the radiation intensity of the white light source 6 that irradiates the object to be measured 9. The z-approximate light source 7 is connected to an additional light source control circuit 12. The additional light source control circuit 12 controls the z-approximate light source 7 in accordance with a control signal output from the signal processing unit 5 to thereby adjust the radiation intensity of a light source that irradiates the object to be measured 9.

Figure 2:
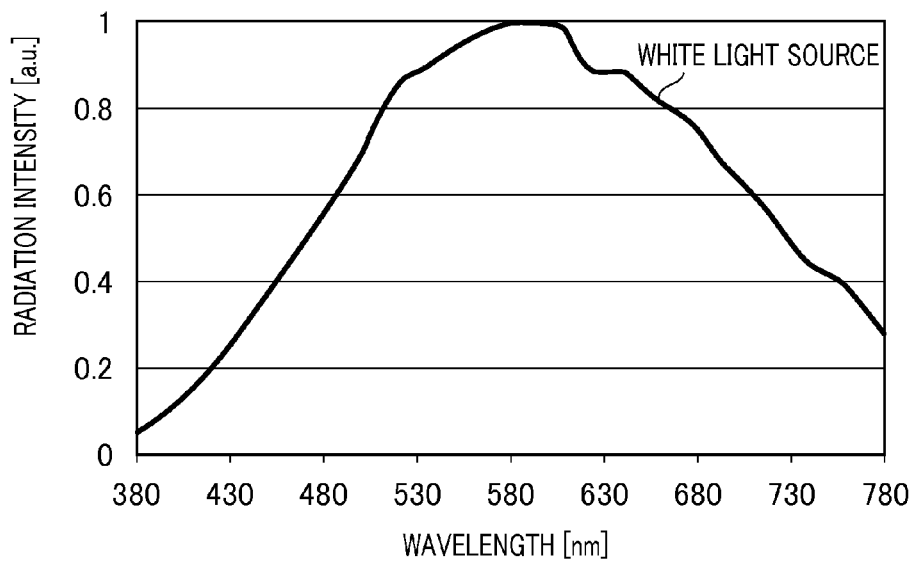
FIG. 2 is a diagram illustrating a spectral intensity distribution of white light according to a first embodiment of the present invention.

FIG. 2 is a diagram illustrating a spectral intensity distribution of the white light source 6, where wavelength is plotted on the horizontal axis and normalized radiation intensity (relative intensity) is plotted on the vertical axis. The white light source 6 has a continuous spectral intensity distribution in which the radiation intensity is not interrupted within the entire visible light region from 380 nm to 780 nm as shown in FIG. 2. It should be noted that, when a white light source to be used has a spectral intensity distribution in which the radiation intensity is present in a region where a wavelength is longer than a visible light region, the radiation intensity in a region where a wavelength is longer than the wavelength of 780 nm is attenuated by the infrared-cut filter 10.

The spectroscope 8 includes a light receiving lens 13, a diffraction grating 14, and a linear sensor 15. The light receiving lens 13 is a lens that receives light emitted from the light sources 7 and 6 and reflected by the object to be measured 9. The diffraction grating 14 disperses light which is incident on the spectroscope 8 via the light receiving lens 13. The linear sensor 15 outputs a signal proportional to the intensity of light which is incident on each element and the spectral sensitivity characteristics of each element and inputs the output signal to the signal processing unit 5.

Next, a detailed description will be given of colorimetry processing performed by the spectrophotometer 1. With reference to FIG. 1, The white light source 6 and the z-approximate light source 7 are disposed such that each light projection angle at which the object to be measured 9 is irradiated is 45 degrees from the direction (vertical direction) normal to the object to be measured 9. Reflected light in the normal direction, which is emitted from the white light source 6 and the z-approximate light source 7 and reflected by the object to be measured 9, is incident on the spectroscope 8 via the light receiving lens 13 and then is dispersed by the diffraction grating 14 serving as a spectroscopic unit. The light dispersed by the diffraction grating 14 is incident on the linear sensor 15 which is a light receiving element. The signal processing unit 5 determines the spectral reflectance of the object to be measured 9 based on the signal input from the linear sensor 15 to thereby determine (calculate) a color value based on the spectral reflectance. The determined color value is output to the display unit 4.

Figure 3:
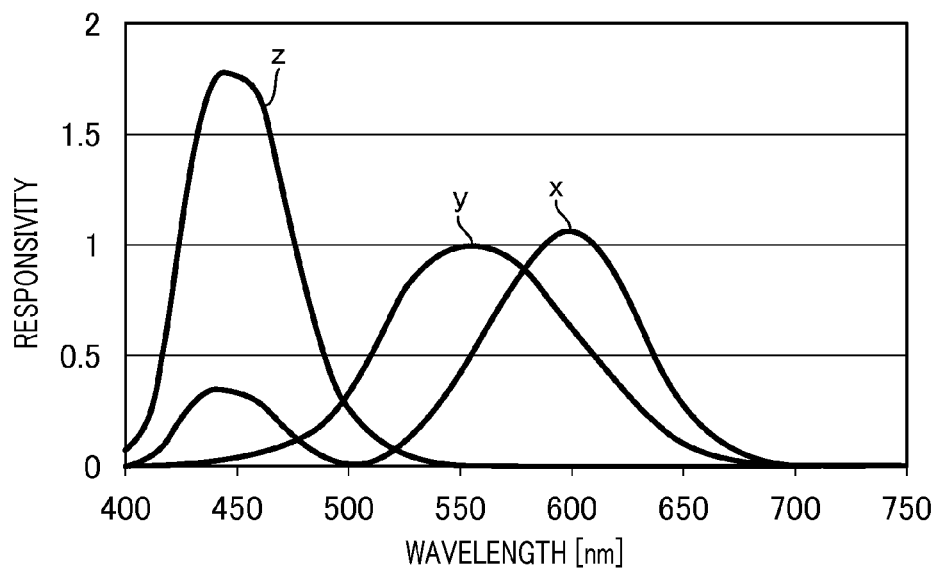
FIG. 3 is a diagram illustrating a color-matching function of an XYZ color system.

Here, in a color value on a uniform color space, a description will be given of the procedure for calculating a color value in an L×a×b×color system (hereinafter referred to as "Lab") which is widely used for color evaluation. FIG. 3 is a diagram illustrating a color-matching function of an XYZ color system, where wavelength is plotted on the horizontal axis and responsivity of each of x, y, and z is plotted on the vertical axis. Firstly, the spectral reflectance of the object to be measured 9 described above is compared to the color-matching function in the XYZ color system shown in FIG. 3 to thereby derive tristimulus values in the XYZ color system. The tristimulus values derived from the spectral reflectance are subject to calculation processing using formula standardized by CIE. By means of calculation processing using the formula, the tristimulus values in the XYZ color system are converted into a color value in the Lab color system. By the above processing, the Lab value which is a color value in a uniform color space is determined as a measured value.

While, in one embodiment of the present invention, an MCU is used as the signal processing unit 5, a DSP (digital signal processor) or an FPGA (field programmable gate array) may also be used instead of an MCU. Also, the light receiving element is configured as the linear sensor 15 but may also be configured as a photodiode or the like. Although the white light source control circuit 11 is provided separately from the additional light source control circuit 12, the same effects can also be obtained even if the white light source control circuit 11 and the additional light source control circuit 12 are configured as a single light source control circuit. Furthermore, although the light source is constituted by both the white light source 6 and the z-approximate light source 7, the light source needs not be necessarily provided in plural, the number of light sources may be one provided that the light source simultaneously exhibits the spectral intensity distributions of the white light source 6 and the z-approximate light source 7.

First Embodiment

A description will be given of a spectrophotometer according to a first embodiment of the present invention.

Firstly, the term "instrumental error" means a color difference which is a difference between color values of a plurality of spectrophotometers. The color difference ΔE×ab (hereinafter referred to as "ΔEab") in the Lab color system can be determined by the following formula using a Lab value:

$$\Delta Eab = \{(\Delta L)^2 + (\Delta a)^2 + (\Delta b)^2\}^{1/2} \quad (1)$$

ΔL is a difference between L-values which are two color values for comparison. Likewise, Δa and Δb are a difference between a-values and b-values which are two color values for comparison, respectively. Here, a description will be given by taking an example in which a color difference ΔEab shown in Formula (1) increases among a plurality of spectrophotometers.

Figure 4:
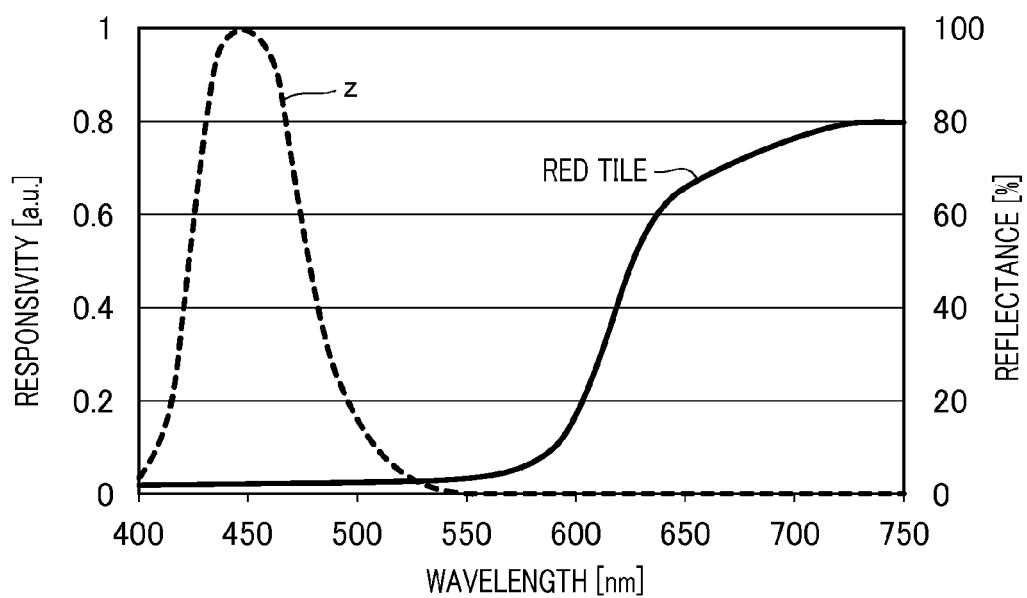
FIG. 4 is a diagram illustrating a color-matching function z in an XYZ color system and a spectral reflectance of a red tile.

FIG. 4 is a diagram illustrating a color-matching function z in an XYZ color system and a spectral reflectance of a BCRA glossy red tile (hereinafter referred to as "red tile") which is widely used as a color standard sheet, where wavelength is plotted on the horizontal axis, the normalized responsivity of the color-matching function z is plotted on the left vertical axis, and the reflectance of the red tile is plotted on the right vertical axis. As shown in FIG. 4, the red tile has a high reflectance in a long wavelength region of 550 nm or longer but has a low reflectance in a wavelength of 450 nm at which the responsivity of the color-matching function z reaches its peak as compared with that in the long wavelength region. Stray light is generated by the spectroscope 8 near a wavelength of 450 nm, and the stray light is undesirably added to net light reflected from the object to be measured 9. The stray light to be generated is caused by a production error of the diffraction grating 14 and the magnitude of stray light differs for each spectroscope 8.

When the reflectance of the object to be measured 9 is low in the entire visible light region, the radiation intensity of the white light source 6 can be increased by the white light source control circuit 11. In this manner, the magnitude of stray light relative to net reflected light can be reduced by increasing the sensor output value in a wavelength of 450 nm.

However, in the case of the red tile, when the radiation intensity of the white light source 6 is increased in order to increase the sensor output value in a wavelength of 450 nm, a sensor output value may undesirably be saturated in a long wavelength region of high reflectance at 550 nm or longer. Thus, a sensor output value in a wavelength of 450 nm cannot be increased so that the magnitude of stray light relative to net reflected light can be increased near a wavelength of 450 nm.

Since the procedure for calculating a Lab value includes comparison processing for comparing the reflectance of the red tile with the color-matching function, a color difference ΔEab increases if an error increases at a wavelength of 450 nm at which the responsivity of the color-matching function z reaches its peak.

As described above, when the reflectance of the object to be measured 9 becomes low at a wavelength of 450 nm at which the responsivity of the color-matching function z reaches its peak and becomes high in a long wavelength region of 550 nm or longer, the difference in the magnitude of stray light between a plurality of spectrophotometers becomes noticeable, resulting in an increase in instrumental error.

Figure 5:
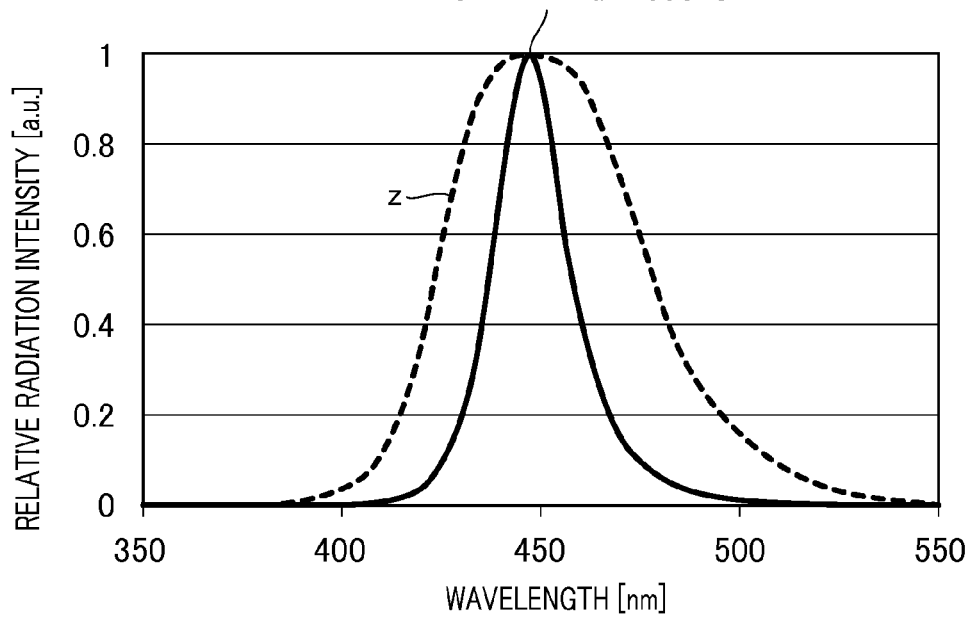
FIG. 5 is a diagram illustrating a color-matching function z in an XYZ color system and a spectral intensity distribution of a z-approximate light source.

Next, a reduction in measurement error caused by stray light in a wavelength of 450 nm will be discussed. FIG. 5 is a diagram illustrating a color-matching function z in an XYZ color system and a spectral intensity distribution of the z-approximate light source 7, where wavelength is plotted on the horizontal axis and relative radiation intensity is plotted on the vertical axis. As shown in FIG. 5, the z-approximate light source 7 selects a light source having an intensity peak at a wavelength of 450 nm in the spectral intensity distribution at which the value (responsivity) of the color-matching function z reaches its peak.

Figure 6:
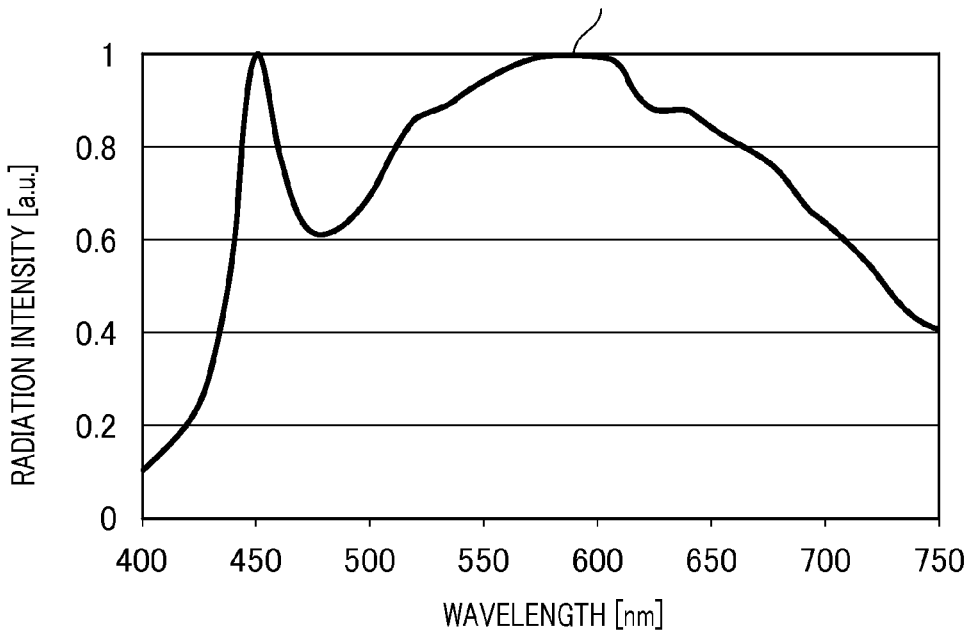
FIG. 6 is a diagram illustrating a spectral intensity distribution obtained when a z-approximate light source is added to a white light source.

FIG. 6 is a diagram illustrating a spectral intensity distribution of a combined light source in which the z-approximate light source 7 is added to the white light source 6, where wavelength is plotted on the horizontal axis and normalized radiation intensity is plotted on the vertical axis. In the spectral intensity distribution shown in FIG. 6 in which the z-approximate light source 7 is added to the white light source 6, the radiation intensity at a wavelength of 450 nm increases about three times as that in the spectral intensity distribution of the white light source 6 shown in FIG. 2. In this manner, even when the object to be measured 9 has a spectral reflectance like that of a red tile, measurement errors at a wavelength of 450 nm can be reduced without saturating a sensor output value. While, in the spectral intensity distribution obtained when the z-approximate light source 7 is added to the white light source 6, a normalized intensity (relative intensity) at a wavelength of 450 nm is set as 1 but the present invention is not limited thereto. Although the effect of the relative intensity may decrease depending on the value thereof, the relative intensity may be a value from 0.5 to 1.

Figure 7A:
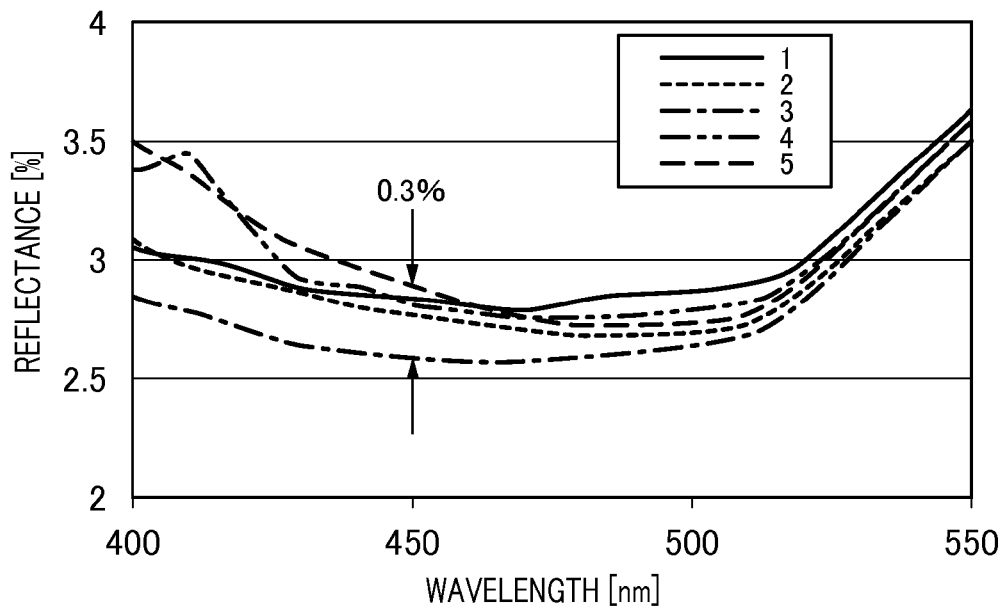
FIGS. 7A and 7B is a diagram illustrating a spectral reflectance of a red tile according to a first embodiment of the present invention.

Next, an instrumental error when the z-approximate light source 7 is added to the white light source 6 will be discussed. FIG. 7A is a diagram illustrating a spectral reflectance of the object to be measured 9, which is calculated based on the signal output from the linear sensor 15, when the object to be measured 9 is a red tile and is irradiated with light only using the white light source 6 having the spectral intensity distribution shown in FIG. 2. In the graph shown in FIG. 7A, wavelength is plotted on the horizontal axis and reflectance is plotted on the vertical axis, and a solid line, a broken line, a single dot chain line, a double dots chain line, and a chain line are values of reflectance obtained when the same red tile is measured by five spectrophotometers. In the graph shown in FIG. 7A, the maximum error of reflectance at a wavelength of 450 nm between five spectrophotometers is 0.3%. When a color difference ΔEab is calculated using the spectral reflectance, an average color difference ΔEab of five spectrophotometers is 0.47.

Figure 7B:
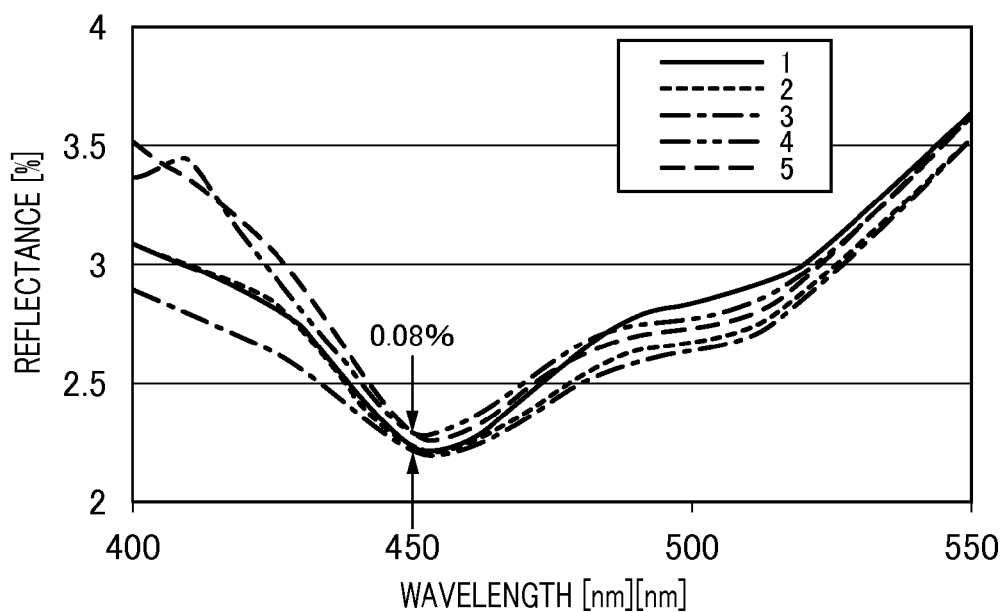

FIG. 7B is a diagram illustrating a spectral reflectance of the object to be measured 9 when the object to be measured 9 is a red tile and is irradiated with light using a combined light source of the white light source 6 and the z-approximate light source 7 having the spectral intensity distribution shown in FIG. 6. As in FIG. 7A, wavelength is plotted on the horizontal axis and reflectance is plotted on the vertical axis. As in FIG. 7A, a solid line, a broken line, a single dot chain line, a double dots chain line, and a chain line are also values of reflectance obtained when the same red tile is measured by five spectrophotometers. In the graph shown in FIG. 7B, the maximum error of reflectance at a wavelength of 450 nm between five spectrophotometers is reduced to 0.08% by the addition of the z-approximate light source 7. When a color difference ΔEab is calculated using the spectral reflectance, an average color difference ΔEab of five spectrophotometers is 0.32. Thus, according to the present embodiment, an instrumental error between spectrophotometers can be reduced by about 30%.

As described above, according to the present embodiment, a spectrophotometer that reduces an instrumental error between a plurality of spectrophotometers may be provided.

Second Embodiment

Next, a description will be given of a spectrophotometer according to a second embodiment of the present invention. The z-approximate light source 7 described in the first embodiment is a light source having an intensity peak at a wavelength of 450 nm in the spectral intensity distribution. In contrast, the z-approximate light source 7 of the spectrophotometer 1 of the present embodiment is a light source having an intensity peak in the wavelength region from 440 nm to 460 nm in the spectral intensity distribution.

The intensity peak in a spectral intensity distribution of LEDs often has an error within ±10 nm from a defined wavelength due to variations in the manufacture of LEDs. Thus, the case where an LED is used as the z-approximate light source 7 and the wavelength at which the intensity in the spectral intensity distribution of the LED reaches its peak is shifted ±10 nm from 450 nm will be discussed.

Figure 8:
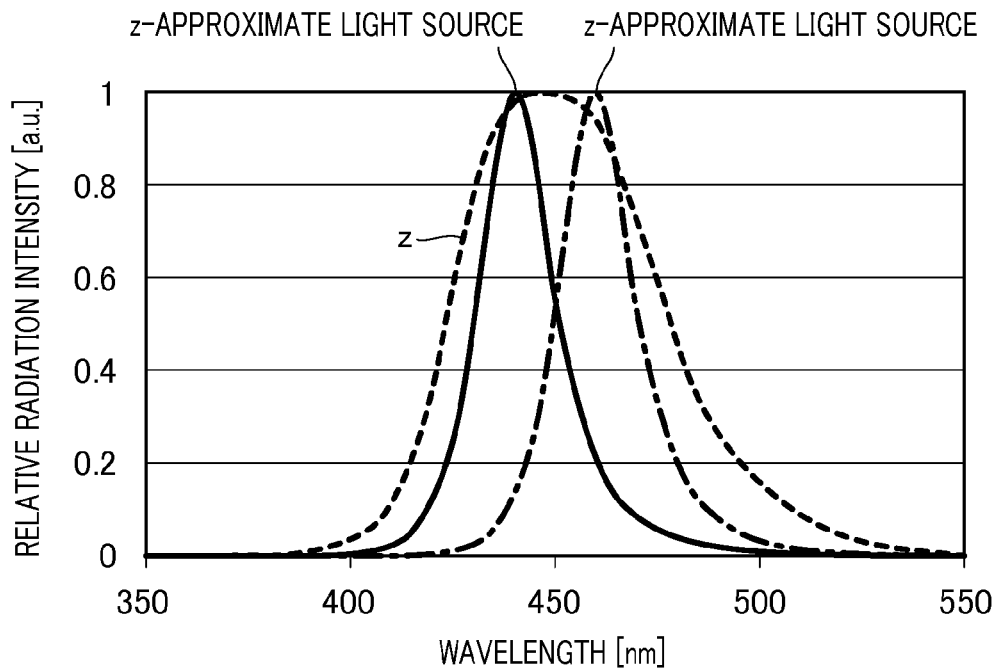
FIG. 8 is a diagram illustrating a color-matching function z in an XYZ color system and a spectral intensity distribution of a z-approximate light source.

FIG. 8 is a diagram illustrating a color-matching function z in an XYZ color system and spectral intensity distributions of two z-approximate light sources 7 each having an intensity peak at a wavelength of 440 nm and 460 nm, respectively, where wavelength is plotted on the horizontal axis and relative radiation intensity is plotted on the vertical axis. A solid line indicates a spectral intensity distribution having an intensity peak at a wavelength of 440 nm and a single dot chain line indicates a spectral intensity distribution having an intensity peak at a wavelength of 460 nm.

In order to reduce an instrumental error between spectrophotometers, measurement error caused by stray light at a wavelength of 450 nm may be reduced. Therefore, even when the wavelength at which the intensity in the spectral intensity distribution of the z-approximate light source 7 reaches its peak is shifted from 450 nm, the relative radiation intensity at a wavelength of 450 nm still needs to be considered.

In the spectral intensity distribution of the z-approximate light source 7 shown in FIG. 8, the relative radiation intensity at a wavelength of 450 nm is about half of its maximum value due to a shift in a wavelength at the peak intensity. Thus, the radiation intensity at a wavelength of 450 nm can be equivalent to the maximum value by setting the radiation intensity relatively equal to or greater than 2 times the radiation intensity of the z-approximate light source 7 having the spectral intensity distribution shown in FIG. 5.

Figure 9:
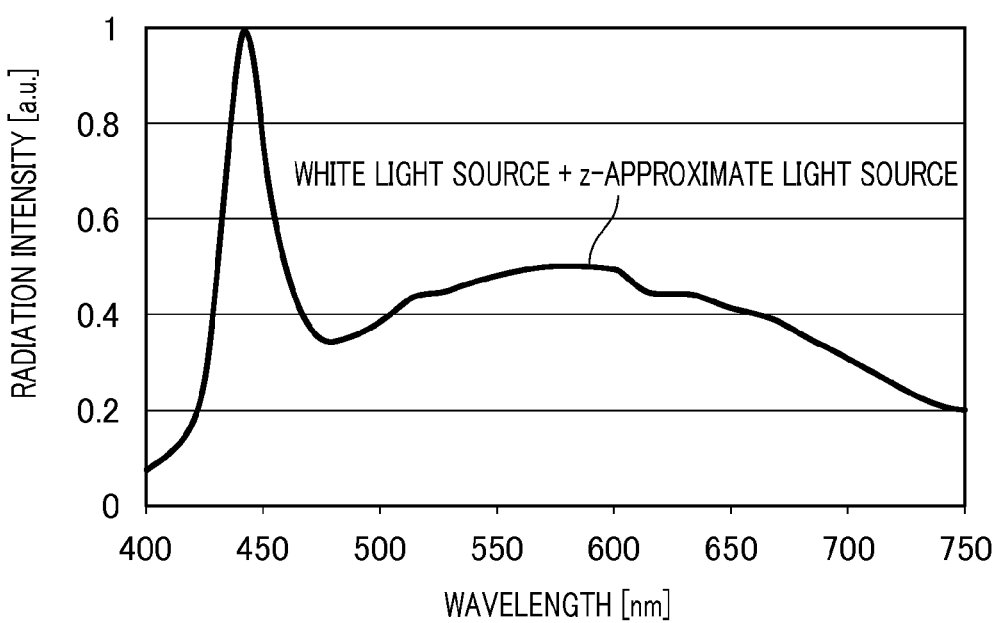
FIG. 9 is a diagram illustrating a spectral intensity distribution obtained when a z-approximate light source is added to a white light source.

FIG. 9 is a diagram illustrating a spectral intensity distribution of a combined light source in which the z-approximate light source 7 having an intensity peak at a wavelength of 440 nm in the spectral intensity distribution is added to the white light source 6, where wavelength is plotted on the horizontal axis and normalized radiation intensity is plotted on the vertical axis. When the wavelength at which the intensity in the spectral intensity distribution of the z-approximate light source 7 reaches its peak is shifted ±10 nm from 450 nm, the radiation intensity of the z-approximate light source 7 may be set relatively equal to or greater than two times the maximum radiation intensity of the white light source 6 as shown in FIG. 9. In this manner, since the radiation intensity at a wavelength of 450 nm is ensured, measurement errors at a wavelength of 450 nm can be reduced without saturating a sensor output value. Also in the present embodiment, an instrumental error between spectrophotometers can be reduced by about 30% as in the first embodiment.

If the radiation intensity may be set relatively equal to or greater than two times as described above, it is apparent that the effect of reduction in instrumental error can be provided even when the wavelength at which the intensity in the spectral intensity distribution of the z-approximate light source 7 reaches its peak is shifted less than 10 nm from 450 nm. Note that, also in the present embodiment, a normalized intensity (relative intensity) at a wavelength of 450 nm in the spectral intensity distribution when the z-approximate light source 7 is added may be a value from 0.5 to 1.

While, in the aforementioned embodiments, the light source of the spectrophotometer 1 is constituted by two light sources, i.e., the white light source 6 and the z-approximate light source 7, the light source of the spectrophotometer 1 may also be constituted by a single light source or three or more light sources provided that the light source has the spectral intensity distribution as shown in FIG. 6 or FIG. 9.

While the embodiments of the present invention have been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-157041 filed on Jul. 13, 2012 which is hereby incorporated by reference herein in its entirety.

What is claimed is:

1. A spectrophotometer that measures a spectral reflectance of an object to be measured and determines a color value of the object to be measured based on a color-matching function of XYZ color system and the measured spectral reflectance, the spectrophotometer comprising:
 an irradiation unit configured to irradiate the object to be measured with light;
 a spectroscope configured to disperse reflected light from the object to be measured; and
 a signal processing unit,
 wherein the irradiation unit comprises:
  a first light source that emits white light; and
  a second light source that emits light having a spectral intensity distribution in which a relative intensity at a wavelength at which a value of z reaches its peak in the color-matching function is equal to or greater than 0.5, and
 wherein the signal processing unit determines:
  the spectral reflectance of the object to be measured based on a signal of light dispersed by the spectroscope,
  a tristimulus value by comparing the spectral reflectance to the color-matching function of the XYZ color system, and
  the color value of the object to be measured based on the tristimulus value of the XYZ color system.

2. The spectrophotometer according to claim 1, wherein the relative intensity is 1.

3. The spectrophotometer according to claim 1, wherein a peak intensity in the spectral intensity distribution of the light emitted from the second light source is equal to or greater than a peak intensity in a spectral intensity distribution of the white light emitted from the first light source.

4. The spectrophotometer according to claim 3, wherein the spectral intensity distribution of the second light source has a peak at a wavelength within the range from 440 nm to 460 nm.

5. The spectrophotometer according to claim 4, wherein the peak intensity in the spectral intensity distribution of light emitted from the second light source is not less than two times of the peak intensity of the first light source.

6. The spectrophotometer according to claim 3, wherein the peak intensity in the spectral intensity distribution of light emitted from the second light source is not less than two times of the peak intensity of the first light source.

* * * * *